(12) United States Patent
Lin

(10) Patent No.: US 7,895,790 B2
(45) Date of Patent: Mar. 1, 2011

(54) ALGAE CULTIVATION APPARATUS

(76) Inventor: Chien-Feng Lin, Hsinchu (TW)

( * ) Notice: Subject to any disclaimer, the term of this patent is extended or adjusted under 35 U.S.C. 154(b) by 169 days.

(21) Appl. No.: 12/428,509

(22) Filed: Apr. 23, 2009

(65) Prior Publication Data
US 2010/0273252 A1    Oct. 28, 2010

(51) Int. Cl.
*A01G 7/00* (2006.01)
*C12M 3/00* (2006.01)
*C12M 1/00* (2006.01)

(52) U.S. Cl. ............... 47/1.4; 435/289.1; 435/292.1

(58) Field of Classification Search ............ 47/1.4; 435/289.1, 292.1
See application file for complete search history.

(56) References Cited

U.S. PATENT DOCUMENTS

| | | | | |
|---|---|---|---|---|
| 4,461,278 A | * | 7/1984 | Mori | 126/700 |
| 4,952,511 A | * | 8/1990 | Radmer | 435/292.1 |
| 4,984,862 A | * | 1/1991 | Mori | 385/31 |
| 5,027,550 A | * | 7/1991 | Mori | 47/1.4 |
| 5,162,051 A | * | 11/1992 | Hoeksema | 47/1.4 |
| 5,958,761 A | * | 9/1999 | Yogev et al. | 435/292.1 |
| 2005/0260553 A1 | * | 11/2005 | Berzin | 435/3 |

* cited by examiner

*Primary Examiner* — Christina Johnson
*Assistant Examiner* — Robert Warden
(74) *Attorney, Agent, or Firm* — Schmeiser, Olsen & Watts, LLP

(57) ABSTRACT

An algae cultivation apparatus includes a light guide plate, at least one transparent circulating channel, at least one light emission module, an algae guide-in module, an algae collection module, a gas guide-in module, a gas collection module, a culture medium guide-in module, a temperature control module and a pH value control module. With the installation of the light guide plate and at least one light emission module, a 24-hour light source can be introduced to improve the production efficiency of an algae.

10 Claims, 3 Drawing Sheets

ALGAE CULTIVATION APPARATUS

FIELD OF THE INVENTION

The present invention relates to an algae cultivation apparatus, in particular to an algae cultivation apparatus for a plant regeneration achieved by a tissue cultivation technology.

BACKGROUND OF THE INVENTION

Industrial revolution brings us a drastic technological development and a fast economic growth and promotes our living of standard significantly, but it also has substantial impacts and damages to the nature. Global surface temperature is climbing gradually to result in a global surface warming phenomenon called "Greenhouse Effect" and caused by a massive quantity of carbon dioxide discharged into the atmosphere. Within the past 150 years, the concentration of carbon dioxide in the atmosphere increases by approximately 25%, and the annual average global temperature rises by 0.5° C. As to the causes of a substantial increase of concentration of carbon dioxide in the atmosphere, our consumption of petroleum fuels is a major cause, in addition to our continuous deforestations. As the world population increases rapidly and the industrial development advances drastically, people are facing a shortage of natural resources including food, energy, minerals and construction materials and an extreme pressure of the ecological environment deterioration. At present, countries all over the world aggressively seek substitute resources to slow down the consumption of natural resources, and prepare for the time when our resources are exhausted in the future. Substitute energies including water power, tide, wind, solar energy and biomass energy and substitute food including fungi, algae and insets are developed at a full speed.

Algae can absorb carbon dioxide through photosynthesis to produce useful constituents such as vitamins, amino acids, pigments, proteins, polysaccharides, celluloses, and fatty acids, etc. In addition, the algae have the advantages of fast growth, high utilization of solar energy, and good nutrition, and thus the algae have become a popular topic of the research of substitute resources. For instance, algae can be used as fodders and substitute food or an agent for processing excessive carbon dioxide, or even an agent for extracting oils from green algae and converting the oils into biodiesels.

Therefore, it is an important subject for scholars and researchers in the related field to quickly cultivate a massive quantity of algae. The algae cultivation primarily requires sufficient light, carbon dioxide and nutrients. To effectively utilize light energy in a cultivation process, we generally use a cultivation device or system to achieve a large light receiving area, a fully mixed cultivation liquid for letting the algae have an effective contact of lights, and allowing the algae to be uniformly in contact with carbon dioxide and nutrients. In addition, a fully mixed cultivation liquid allows the algae to produce oxygen efficiently and prevents the algae from attaching onto the surface of the cultivation device that may result in a low light transmission rate of the cultivation device.

In past decades, many algae cultivation apparatuses and methods were introduced. For instance, a pool type photosynthesis reactor was used at the early stage for cultivating algae, and the structure of the pool type photosynthesis reactor is a water pool having a depth of approximately 15~20 cm, and ventilations are provided at the bottom of the pool to promote circulation and mixing. The photosynthesis reactors of this sort come with a simple structure, an easy manufacture and a low cost, but the mixed nutrients are not uniform, and the algae generally sink to the bottom of the pool, so that this structure is replaced by canal type photosynthesis reactor. In a canal type photosynthesis reactor, the cultivation liquid is flowing, and a turbulent current produced between the fluid and the channel walls can provide the effects of mixing the cultivation liquid and suspending the cells. Thus, the cell growth curve of a general channel type photosynthesis reactor is much better than that of the pool type photosynthesis reactor.

However, the aforementioned photosynthesis reactors are outdoor open systems, which have the advantages of a low cost and a capability for a large-scale cultivation, but they also have the disadvantages of a too-large area that may be contaminated by other organisms or dust and affected by the weather easily. Furthermore, carbon dioxide may be leaked easily. Thus, a close cultivation system was introduced later. At present, the close cultivation systems include fermentation tanks, pipe type photosynthesis reactors, sheet type photosynthesis reactors, and spiral pipe type photosynthesis reactors, etc. The spiral pipe type photosynthesis reactor is a pipe type photosynthesis reactor bent into a spiral shape, and thus it has a longer reaction path, and a longer distance for exchanging more fluids to assist algae to gain sufficient carbon dioxide in the photosynthesis reactor. In addition, the pipe type photosynthesis reactor also has a larger backlight area for maximizing the utilization of light. The close cultivation system has the advantages of providing an easy control of environmental factors, a good resistance to contamination, and a high cultivation density, but also has the disadvantages of incurring a high cost and an easy damage to pipes by earthquakes.

Therefore, it is the most important subject of the present invention to design and develop an algae cultivation apparatus having with the advantages of an easy manufacture, a low cost, a flexible operation, a high production efficiency and a 24-hour supply of light source as well as cultivating a massive quantity of required algae.

SUMMARY OF THE INVENTION

In view of the shortcomings of the conventional algae cultivation apparatus, the inventor of the present invention based on years of experience in the related industry to conduct extensive researches and experiments, and finally developed an algae cultivation apparatus, in hope of achieving the advantages of an easy manufacture, a low cost, a flexible operation, a high production efficiency and a 24-hour supply of light source as well as cultivating a massive quantity of a required alga.

Therefore, it is a primary objective of the present invention to provide an algae cultivation apparatus, comprising: a light guide plate, made of a transparent material; at least one transparent circulating channel, having a first portion and a second portion, wherein the first portion is installed continuously in a S-shape and disposed on the light guide plate, and the second portion is connected to the first portion by a head-and-tail connection to complete a cycle, wherein the surface of the transparent circulating channel is a cambered surface, and both head and tail of the first portion have an opening individually; at least one light emission module, installed on a side of the light guide plate; an algae guide-in module, connected to a head opening of the first portion, for guiding in an alga; an algae collection module, connected to a tail opening of the first portion, for collecting algae; a gas guide-in module, connected to a tail opening of the first portion, for guiding a processing gas into collecting algae in the transparent circulating channel; a gas collection module, connected to a head opening of the first portion, for collecting gases produced in the transparent circulating channel; a culture medium guide-in module, for guiding a culture medium into the transparent circulating channel; a temperature control module, for controlling the temperature of the transparent circulating channel; and a pH value control module, for controlling the pH value of the transparent circulating channel.

Therefore, an algae cultivation apparatus of the present invention can achieve the advantages of an easy manufacture, a low cost, a flexible operation, a high production efficiency and a 24-hour supply of light source as well as cultivate a massive quantity of a required alga.

DESCRIPTION OF THE PREFERRED EMBODIMENTS

Other features and advantages of the present invention will become apparent in the following detailed description of the preferred embodiments with reference to the accompanying drawings.

Figure 1:
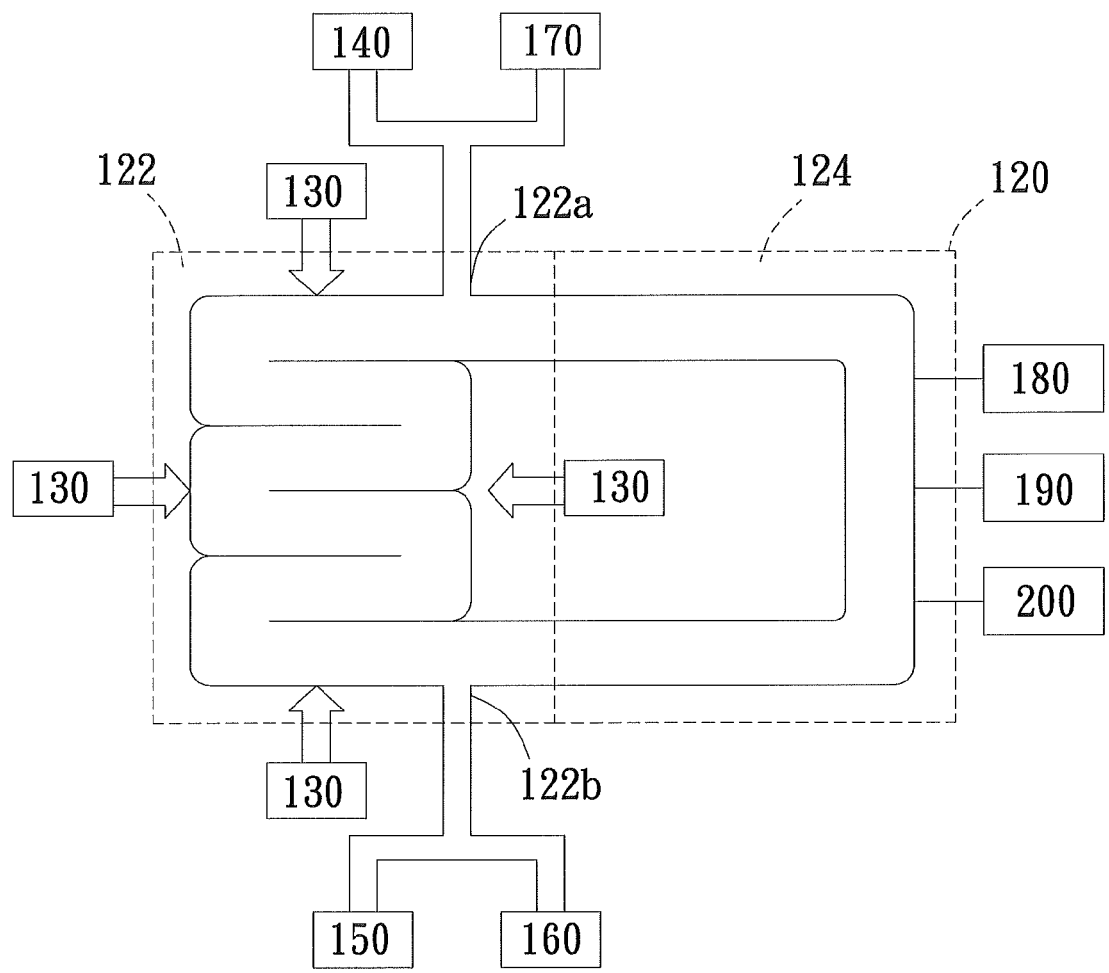
FIG. 1 is a front view of an algae cultivation apparatus in accordance with a preferred embodiment of the present invention.
Figure 2:
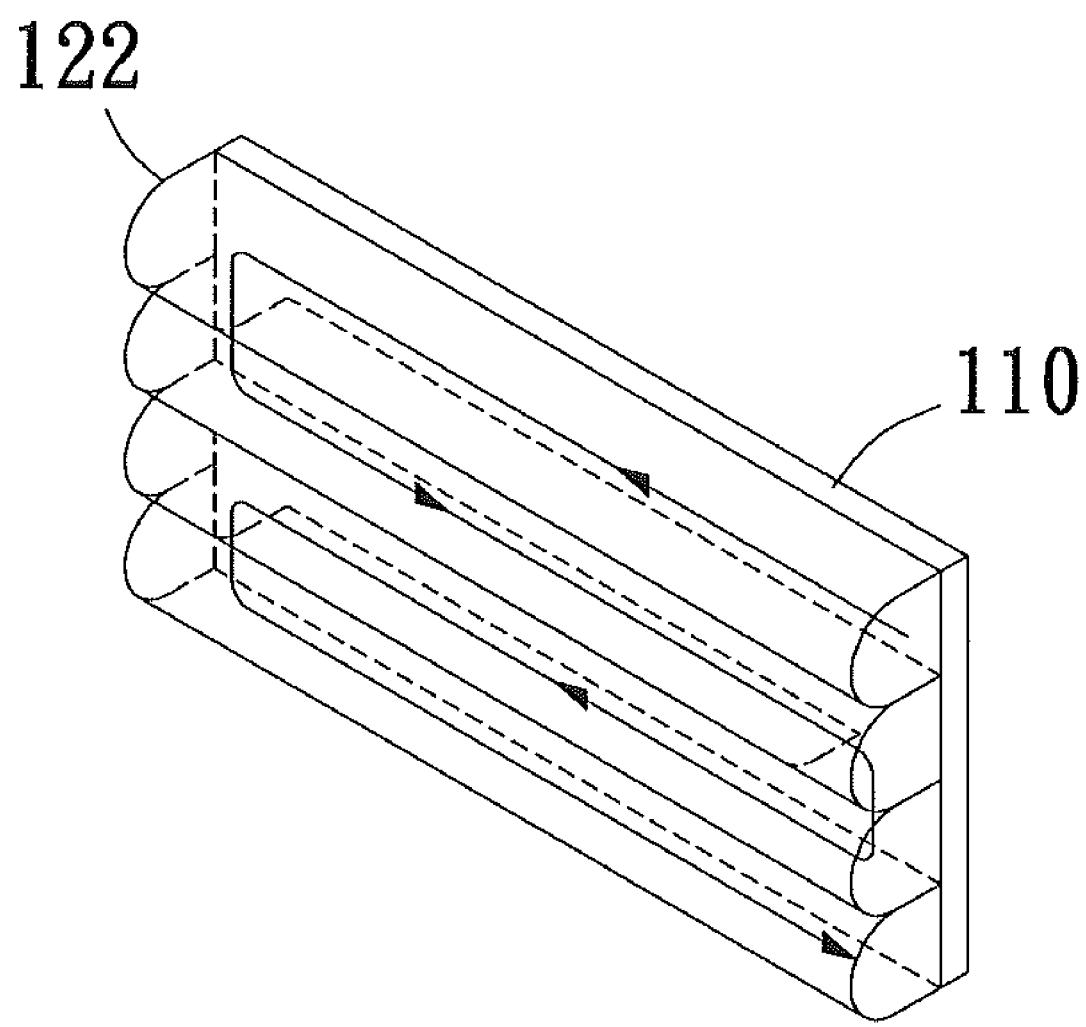
FIG. 2 is a perspective view of a first portion of a transparent circulating channel in accordance with a preferred embodiment of the present invention.
Figure 3A:
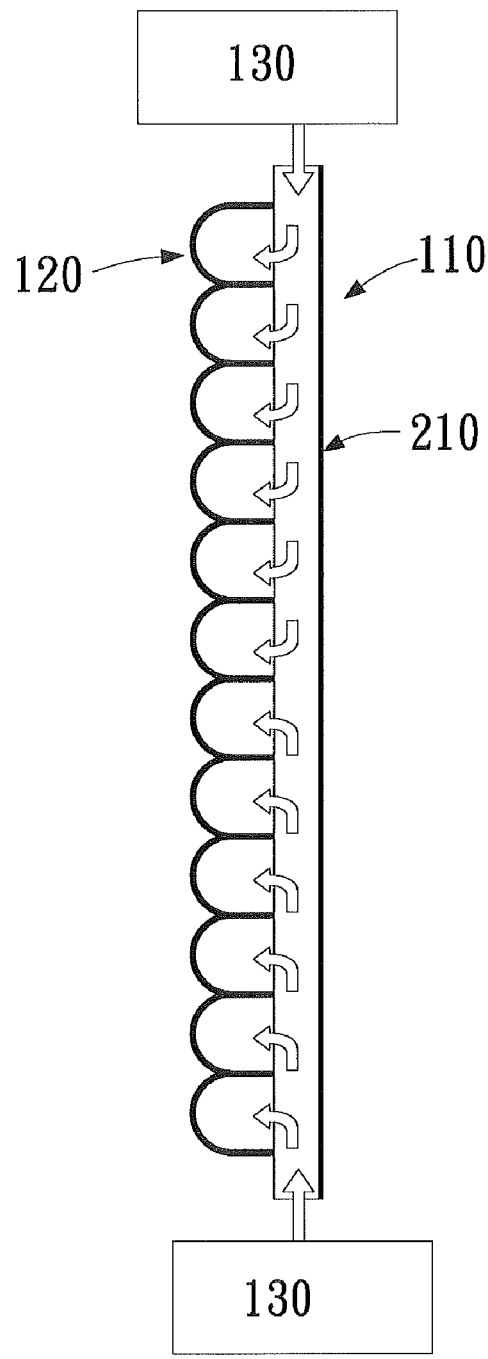
FIG. 3A is a side view of an algae cultivation apparatus in accordance with a preferred embodiment of the present invention.

With reference to FIGS. 1, 2 and 3A, FIG. 1 shows a front view of an algae cultivation apparatus in accordance with a preferred embodiment of the present invention, FIG. 2 shows a perspective view of a first portion of a transparent circulating channel in accordance with a preferred embodiment of the present invention, and FIG. 3A shows a side view of an algae cultivation apparatus in accordance with a preferred embodiment of the present invention. The algae cultivation apparatus in accordance with a preferred embodiment of the present invention comprises a light guide plate 110, a transparent circulating channel 120, a light emission module 130, an algae guide-in module 140, an algae collection module 150, a gas guide-in module 160, a gas collection module 170, a culture medium guide-in module 180, a temperature control module 190, a pH value control module 200 and a light reflecting plate 210.

The light guide plate 110 is made of a transparent material for guiding light. The transparent circulating channel 120 has a first portion 122 and a second portion 124, and the first portion 122 is installed in a continuous S-shape and disposed on the light guide plate 110, and the second portion 124 is connected to the first portion 122 by a head-and-tail connection to complete a cycle, wherein the surface of the transparent circulating channel 120 is a cambered surface, and both head and tail of the first portion 122 have an opening 122a, 122b individually. The cambered surface of the transparent circulating channel 120 can prevent algae stored in the transparent circulating channel 120 from being stuck at dead corners and allow the algae to be removed easily. The light emission module 130 is installed on at least one side of the light guide plate 110, and the light emission module 130 can be a red LED module with a wavelength of 620~685 nm, a blue LED module with a wavelength of 440~485 nm, or a light guide module for collecting sunlight by optical fibers. A light reflecting plate 210 is installed on another side of the light guide plate 110, such that the light projected from the light emission module 130 to the light guide plate 110 can be utilized completely.

Therefore, the algae of the present invention can be projected with sufficient sunlight that passes through at least one side of the light guide plate 110 and the transparent circulating channel 120. At nighttime or in a dark environment, the light emission module 130 is started to provide sufficient light through the light guide plate 110 and the light reflecting plate 210, so as to achieve the effect of providing a 24-hour light source.

The algae guide-in module 140 is connected to a head opening 122a of the first portion 122 for guiding in algae. The algae collection module 150 is connected to a tail opening 122b of the first portion 122, for collecting algae. With the effect of the gravitational force, the present invention can easily guide immature algae in from the top of the opening and mature algae out from the bottom of the opening.

The gas guide-in module 160 is connected to the tail opening 122b of the first portion 122, for guiding a processing gas into the transparent circulating channel 120, wherein the processing gas is carbon dioxide. The gas collection module 170 is connected to the head opening 122a of the first portion 122, for collecting gases produced in the transparent circulating channel 120. By the principle of a gas floating in a liquid, the present invention can guide and scatter the processing gas from the bottom into all transparent circulating channels and guide the produced gas from the top to the outside for a gas collection.

The culture medium guide-in module 180 is used for guiding a culture medium into the transparent circulating channel 120, wherein the culture medium guided by the culture medium guide-in module can be a nitrate, a phosphate or a vitamin. The temperature control module 190 is used for controlling the temperature of the transparent circulating channel 120. The pH value control module 200 is used for controlling the pH value of the transparent circulating channel 120. With the aforementioned three modules 180, 190, 200, the growth of algae can be controlled effectively to achieve a flexible operation and a high production efficiency of algae for the present invention.

Figure 3B:
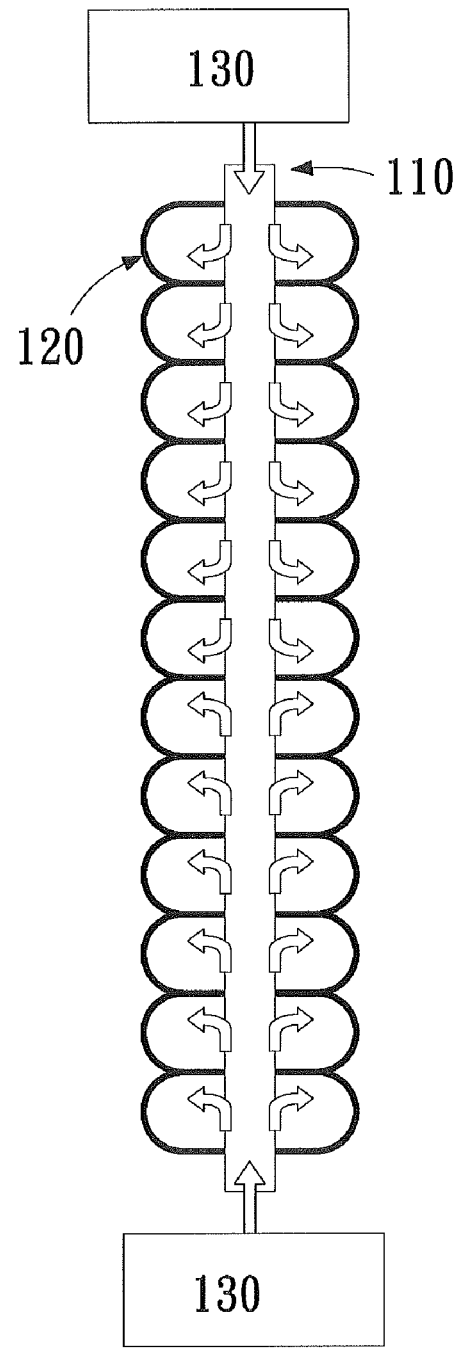
FIG. 3B is a side view of an algae cultivation apparatus in accordance with another preferred embodiment of the present invention.

With reference to FIG. 3B for a side view of an algae cultivation apparatus in accordance with another preferred embodiment of the present invention, the transparent circulating channel 120 is installed on both sides of the light guide plate 110 individually, so that the algae cultivation apparatus in accordance with this preferred embodiment of the present invention incurs a higher cost, but doubles the production efficiency, and thus the invention can be applied freely depending on the user requirements.

In summation of the description above, the present invention complies with the patent application requirements, and the present invention installs a light guide plate, at least one transparent circulating channel, at least one light emission module, an algae guide-in module, an algae collection module, a gas guide-in module, a gas collection module, a culture medium guide-in module, a temperature control module and a pH value control module to provide the advantages of an easy manufacture, a low cost, a flexible operation, a high production efficiency and a 24-hour supply of light source. Thus, the present invention can achieve the effect of cultivating a massive quantity of required algae quickly and meet the current market requirements fully.

While the invention has been described by means of specific embodiments, numerous modifications and variations could be made thereto by those skilled in the art without departing from the scope and spirit of the invention set forth in the claims.

What is claimed is:

1. An algae cultivation apparatus, comprising:
   a light guide plate, made of a transparent material;
   at least one transparent circulating channel, having a first portion and a second portion, and the first portion being installed in a continuous S-shape and disposed on the light guide plate, and the second portion being connected to the first portion by a head-and-tail connection to complete a cycle, and the surface of the transparent circulating channel being a cambered surface, and both head and tail of the first portion having an opening individually;
   at least one light emission module, installed on at least one side of the light guide plate;
   an algae guide-in module, connected to the head opening of the first portion, for guiding in an alga;
   an algae collection module, connected to the tail opening of the first portion, for collecting an alga;
   a gas guide-in module, connected to the tail opening of the first portion, for guiding a processing gas into the transparent circulating channel;
   a gas collection module, connected to the head opening of the first portion, for collecting a gas produced in the transparent circulating channel;
   a culture medium guide-in module, for guiding a culture medium into the transparent circulating channel;
   a temperature control module, for controlling the temperature of the transparent circulating channel; and
   a pH value control module, for controlling the pH value of the transparent circulating channel.

2. The apparatus of claim 1, wherein the light guide plate further includes a light reflecting plate installed on another side of the light guide plate, if the quantity of transparent circulating channel is one.

3. The apparatus of claim 2, wherein the light emission module is an LED module or a light guide module for collecting sunlight through an optical fiber.

4. The apparatus of claim 3, wherein the LED module is a red LED module with a wavelength of 620~685 nm.

5. The apparatus of claim 3, wherein the LED module is a blue LED module with a wavelength of 440~485 nm.

6. The apparatus of claim 1, wherein the light emission module is an LED module or a light guide module for collecting sunlight through an optical fiber.

7. The apparatus of claim 6, wherein the LED module is a red LED module with a wavelength of 620~685 nm.

8. The apparatus of claim 6, wherein the LED module is a blue LED module with a wavelength of 440~485 nm.

9. The apparatus of claim 1, wherein the gas guided by the gas guide-in module is carbon dioxide.

10. The apparatus of claim 1, wherein the culture medium guided by the culture medium guide-in module is a nitrate, a phosphate or a vitamin.

* * * * *